(12) United States Patent
Knauper et al.

(10) Patent No.: US 7,534,099 B2
(45) Date of Patent: May 19, 2009

(54) ALIQUOT CORRECTION FOR FEEDING SET DEGRADATION

(75) Inventors: Christopher A. Knauper, O'Fallon, MO (US); Eric B. Holderle, St. Louis, MO (US); Joseph A. Hudson, O'Fallon, MO (US)

(73) Assignee: Covidien AG (CH)

( * ) Notice: Subject to any disclaimer, the term of this patent is extended or adjusted under 35 U.S.C. 154(b) by 590 days.

(21) Appl. No.: 11/240,956

(22) Filed: Sep. 30, 2005

(65) Prior Publication Data

US 2007/0077152 A1   Apr. 5, 2007

(51) Int. Cl.
F04B 43/08 (2006.01)
(52) U.S. Cl. .................................... 417/477.1; 700/282
(58) Field of Classification Search ................ 417/44.1, 417/477.1, 477.12; 72/453.01; 700/281, 700/282; 702/45, 100
See application file for complete search history.

(56) References Cited

U.S. PATENT DOCUMENTS

| | | | |
|---|---|---|---|
| 3,737,251 A | 6/1973 | Berman et al. | |
| 3,982,540 A | 9/1976 | Ross | |
| 4,213,454 A | 7/1980 | Shim | |
| 4,346,705 A * | 8/1982 | Pekkarinen et al. | 604/30 |
| 4,529,401 A | 7/1985 | Leslie et al. | |
| 4,634,246 A | 1/1987 | Dreyer, Jr. | |
| 4,660,607 A | 4/1987 | Griffith et al. | |
| 4,817,044 A | 3/1989 | Ogren | |
| 5,018,945 A | 5/1991 | Silva | |
| 5,041,086 A | 8/1991 | Koenig et al. | |
| 5,181,910 A | 1/1993 | Scanlon | |
| 5,237,309 A | 8/1993 | Frantz et al. | |
| 5,318,519 A | 6/1994 | Wilk | |
| 5,482,438 A | 1/1996 | Anderson et al. | |
| 5,482,446 A | 1/1996 | Williamson et al. | |
| 5,628,619 A | 5/1997 | Wilson | |
| 5,630,710 A | 5/1997 | Tune et al. | |
| 5,649,810 A | 7/1997 | Schweitzer, Jr. et al. | |
| 5,658,133 A | 8/1997 | Anderson et al. | |
| 5,658,250 A | 8/1997 | Blomquist et al. | |
| 5,755,563 A | 5/1998 | Clegg et al. | |
| 5,791,880 A | 8/1998 | Wilson | |
| 5,853,387 A | 12/1998 | Clegg et al. | |
| 5,915,408 A * | 6/1999 | Dudley | 137/244 |
| 6,076,522 A | 6/2000 | Dwivedi et al. | |
| 6,254,567 B1 | 7/2001 | Treu et al. | |
| 6,267,570 B1 | 7/2001 | Armando | |

(Continued)

FOREIGN PATENT DOCUMENTS

EP          0 458 910         12/1991

(Continued)

Primary Examiner—Devon C Kramer
Assistant Examiner—Dnyanesh Kasture
(74) Attorney, Agent, or Firm—Edward S. Jarmolowicz, Esq

(57) ABSTRACT

A peristaltic pump is able to deliver accurate volumes over the life of a pump set that is operated on by the pump to drive the flow of fluid. The pump delivers fluid in small volumes or aliquots. In order to deliver fluid at any particular selected flow rate, the pump determines how often the rotor will rotate. The pump is able to calculate aliquot volume based on selected flow rate, but also on a factor that compensates for changes in the dimensions of the pump set over its life.

23 Claims, 7 Drawing Sheets

U.S. PATENT DOCUMENTS

| | | |
|---|---|---|
| 6,371,732 B1 | 4/2002 | Moubayed et al. |
| 6,449,532 B1 | 9/2002 | Nicol |
| 6,464,687 B1 | 10/2002 | Ishikawa et al. |
| 6,491,663 B1 | 12/2002 | Lemelson |
| 6,495,366 B1 | 12/2002 | Briggs |
| 6,565,535 B2 | 5/2003 | Zaias et al. |
| 6,588,632 B1 | 7/2003 | Nicol |
| 6,604,054 B2 | 8/2003 | Lipscomb et al. |
| 6,659,976 B2 | 12/2003 | Beck et al. |
| 7,270,013 B2 * | 9/2007 | Bhullar et al. ............... 73/861 |
| 7,396,512 B2 * | 7/2008 | DiTrolio et al. ............. 422/100 |
| 2004/0225252 A1 | 11/2004 | Gillespie, Jr. et al. |
| 2005/0082237 A1 | 4/2005 | Dolecek et al. |
| 2005/0206340 A1 | 9/2005 | Brundle et al. |
| 2006/0184121 A1 | 8/2006 | Brockman et al. |

FOREIGN PATENT DOCUMENTS

| | | |
|---|---|---|
| EP | 1473050 A1 | 11/2004 |
| GB | 2 207 196 A | 1/1989 |
| WO | WO 82/01320 A | 4/1982 |
| WO | 9217226 A2 | 10/1992 |

* cited by examiner

ALIQUOT CORRECTION FOR FEEDING SET DEGRADATION

BACKGROUND

This invention relates generally to peristaltic pumps used to deliver fluids to patients by way of a pump set, and more particularly to a peristaltic pump that compensates for physical alteration of the pump set over time to maintain accuracy.

Administering fluids containing medicine or nutrition to a patient is well known in the art. Typically, fluid is delivered to the patient by a pump set loaded on a flow control apparatus, such as a peristaltic pump, which delivers fluid to the patient at a controlled rate of delivery. A peristaltic pump usually comprises a housing that includes a rotor or the like operatively engaged to at least one motor through a gearbox. The rotor drives fluid through the tubing of the pump set by the peristaltic action effected by rotation of the rotor by the motor. The motor is operatively connected to a rotatable shaft that drives the rotor, which in turn progressively compresses the tubing and drives the fluid at a controlled rate through the pump set. The pump set may have a type of valve mechanism for permitting or preventing fluid flow communication through the pump set. A controller operates the motor or motors used to drive the rotor and, if necessary, control fluid flow as by operation of the valve mechanism.

Peristaltic pumps operate by delivering fluid in small charges called "aliquots". The rotor engages tubing of the pump set, pinching off a portion of the tubing and pushing fluid forward of the pinch point (i.e., closer to the patient than to the source of fluid) toward the patient. Typically, the volume of fluid to be administered to the patient is controlled in the pump by counting the number of aliquots, each being of substantially the same volume, and stopping when the number reaches an amount corresponding to the total desired volume of fluid to be delivered. Peristaltic pumps are sanitary and generally highly accurate and therefore very useful in the administration of medication and therapeutic fluids to the patient. However, the accuracy of the pump is dependent upon the dimensional stability of the tubing of the pump set. Over time the pump set can be plastically deformed so that the volume of each aliquot can change. As a result, the accuracy of the volumes delivered to the patient degrades over the course of the life of the pump set. By way of example, an administration feeding set used for enteral feeding may be used for up to 24 hours.

SUMMARY OF INVENTION

In one aspect of the present invention, a pumping apparatus for use with a pump set to deliver fluid through the pump set generally comprises a pumping device capable of acting on the pump set to produce a fluid flow within the pump set. The pumping device produces the fluid flow in a series of aliquots. A housing is capable of receiving at least a portion of the pump set to be acted upon by the pumping device. A controller programmed to control an electrical signal to the pumping device includes a pump set degradation compensator for changing the electrical signal thereby altering operation of the pumping device. As a result, the fluid flow rate delivered by the pumping apparatus is more accurate over the useful life of the pump set.

In another aspect of the present invention, a method of delivering accurate desired flow rates of fluid using a pumping apparatus that acts on a pump set attached to the pumping apparatus to produce flow of fluid in aliquots generally comprises determining the amount of time the pump set has been in use in the pumping apparatus. The volume of fluid in each aliquot delivered by the pumping apparatus is calculated including executing instructions that are capable of correcting the aliquot volume based on the amount of time the pump set has been in use in the pumping apparatus. The pumping apparatus is operated to deliver a number of aliquots having the aliquot volume determined in the preceding step to maintain a selected flow rate.

Other objects and features of the present invention will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION

Figure 1:
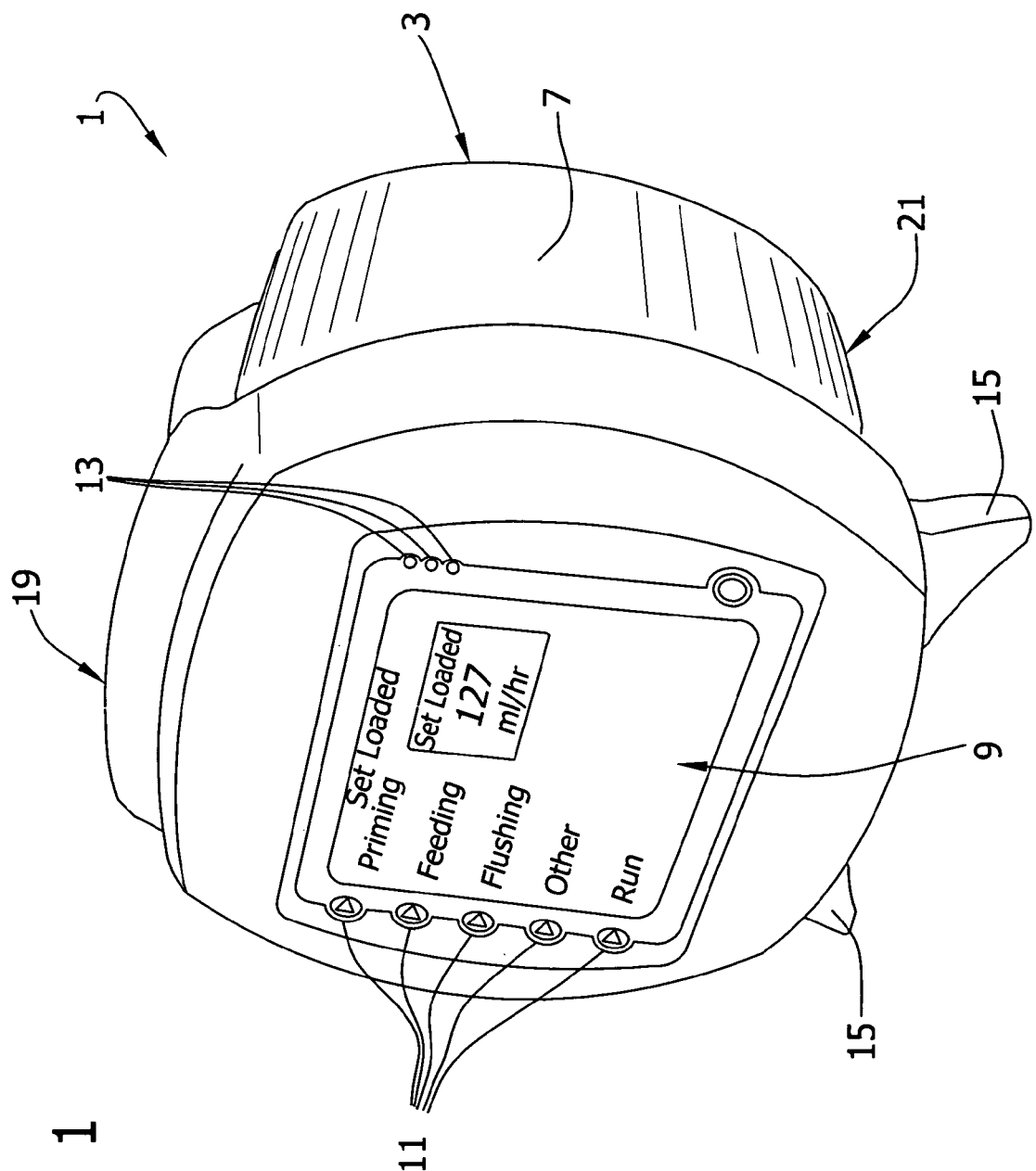
FIG. 1 is a perspective of an enteral feeding pump.
Figure 2:
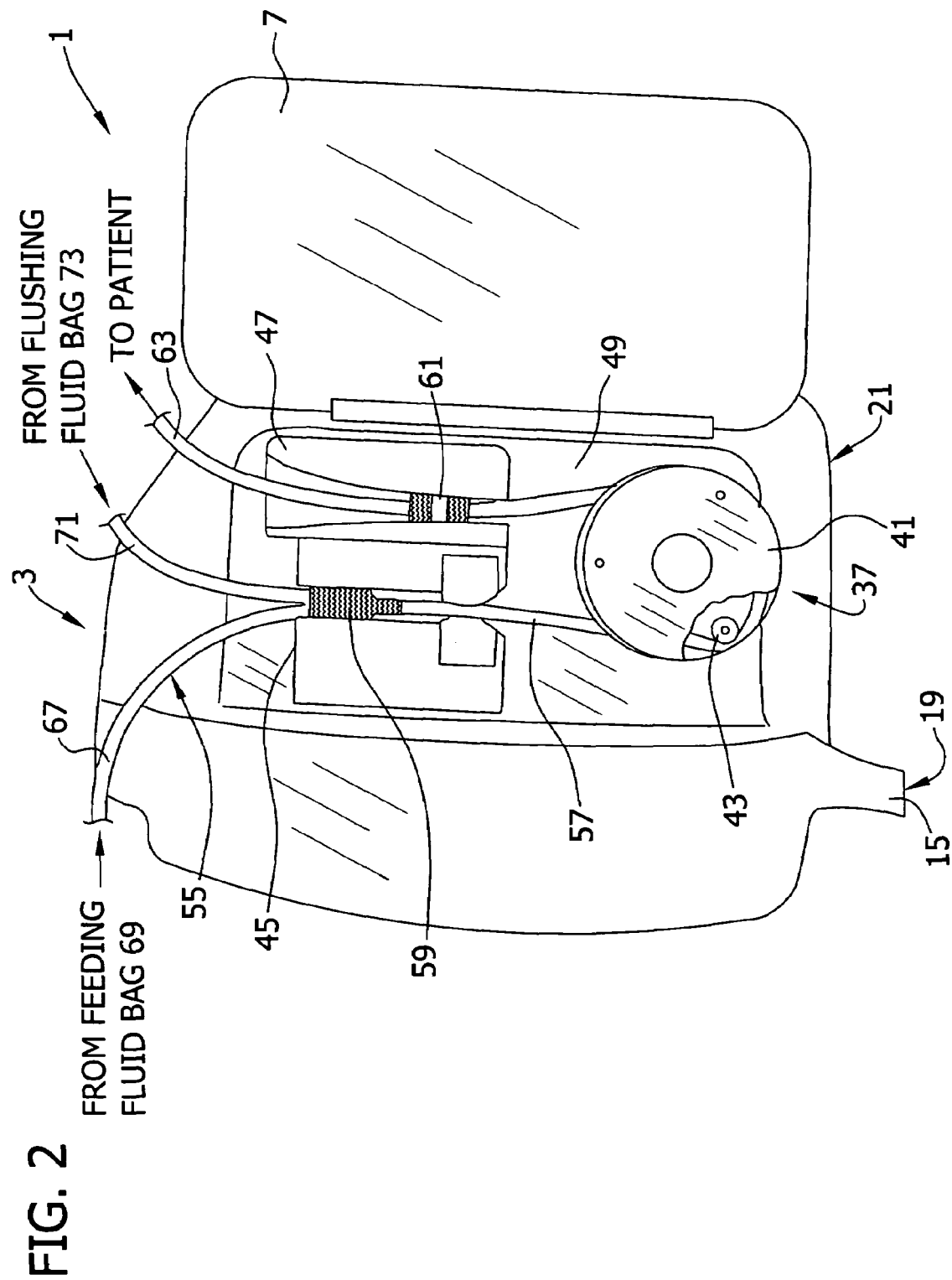
FIG. 2 is a side elevation thereof showing a fragmentary portion of an administration feeding set received in the pump.

Referring now to the drawings, an enteral feeding pump (broadly, "flow control apparatus") constructed according to the principles of the present invention is generally indicated at 1. The feeding pump comprises a housing generally indicated at 3 that is constructed so as to mount an administration feeding set (broadly, a "pump set") generally indicated at 5 (see FIGS. 2 and 5). The housing 3 includes a door 7 hinged to the remainder of the housing for swinging between a closed position (FIG. 1) and an open position (FIG. 2) which exposes a portion of the pump 1 that receives the administration feeding set 5. It will be appreciated that "housing" as used herein may include many forms of supporting structures (not shown), including without limitation multi-part structures and structures that do not enclose or house the working components of the pump 1. The pump 1 also has a display screen generally indicated at 9 on the front of the housing 3 that is capable of displaying information about the status and operation of the pump. Buttons 11 on the side of the display screen 9 are provided for use in controlling and obtaining information from the pump 1 and three light emitting diodes 13 also provide status information for the pump. Legs 15 at the bottom front of the housing 3 support the housing so that the display screen 9 is angled slightly upward for ease of viewing.

It will be understood that although the illustrated pump 1 is an enteral feeding pump, the present invention has application to other types of peristaltic pumps (not shown), including medical infusion pumps. The general construction and operation of the enteral feeding pump 1, except as set forth hereinafter, may be generally the same as disclosed in co-assigned U.S. patent application Ser. No. 10/853,958 filed May 24, 2004 and entitled ADMINISTRATION FEEDING SET AND VALVE MECHANISM, Ser. No. 10/854,136 filed May 24, 2004 and entitled FLOW CONTROL APPARATUS, and Ser. No. 10/853,926 filed May 25, 2004 entitled FLOW MONITORING SYSTEM FOR A FLOW CONTROL APPARATUS, the disclosures of which are incorporated by reference. Moreover, although an administration feeding set 5 is shown, other types of pump sets (not shown) can be used within the scope of the present invention.

Figure 3:
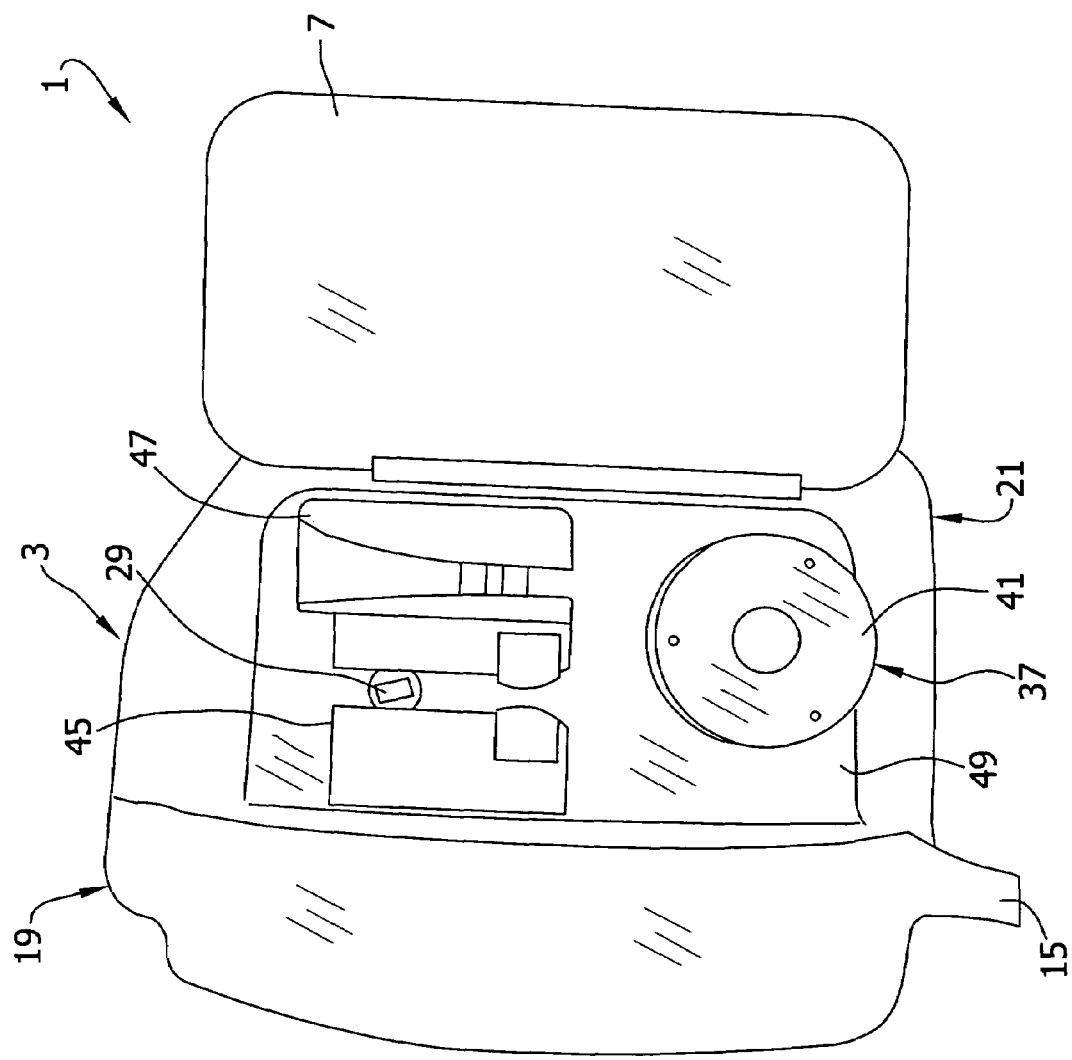
FIG. 3 is the side elevation of FIG. 2 with the administration feeding set removed.
Figure 4:
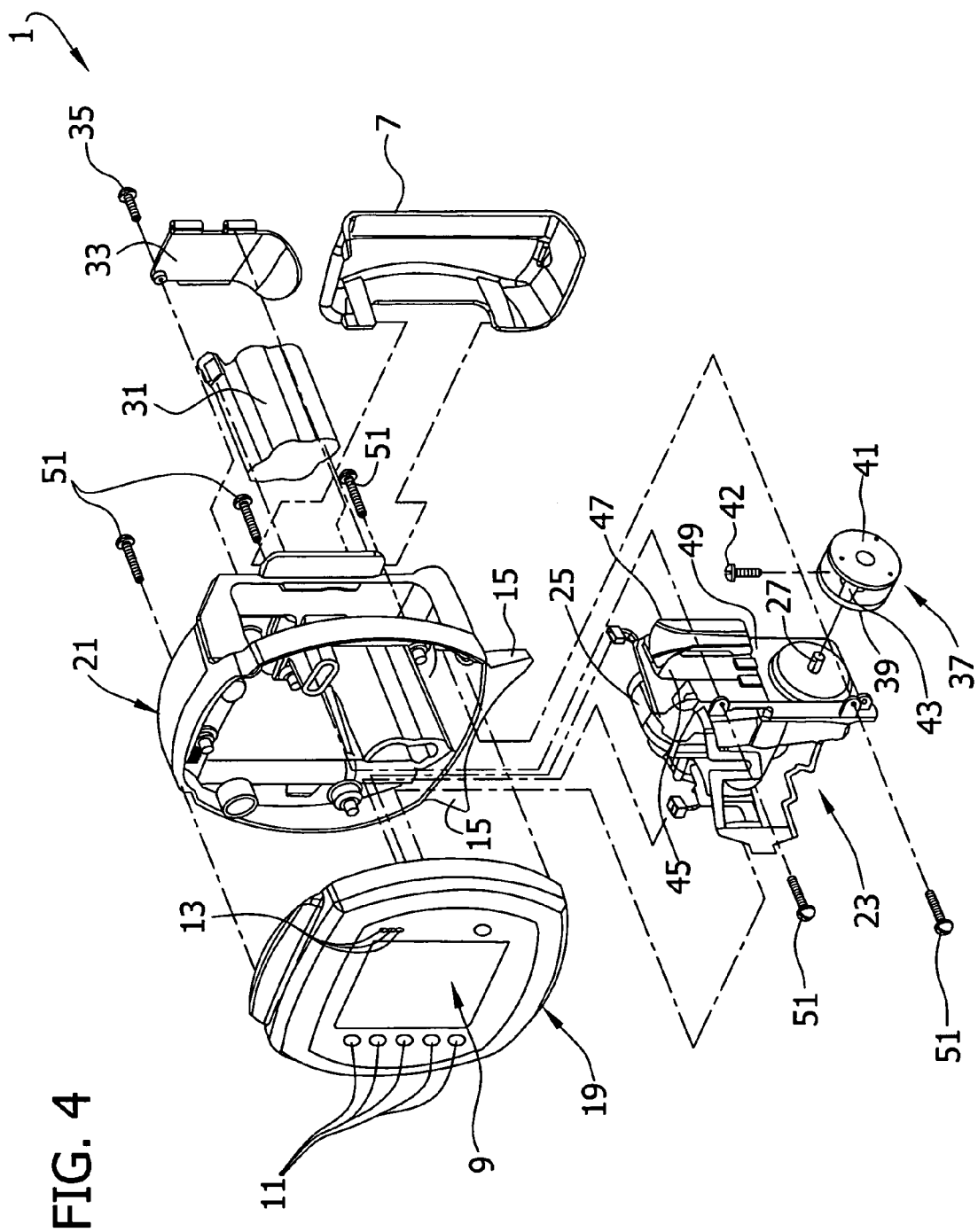
FIG. 4 is an exploded perspective of the pump.

Referring now also to FIG. 4, the display screen 9 is part of a front panel (generally indicated at 19) of the housing 3 removably attached to a main compartment (generally indicated at 21) of the housing that holds most of the operating components of the pump 1. The enteral feeding pump further includes a pumping unit (shown exploded from the main compartment and indicated generally at 23) comprising a pump motor 25 connected to a rotor shaft 27 and also to a valve shaft 29 (see, FIG. 3). It will be understood that the valve shaft 29 could be omitted, and/or that a separate motor (not shown) could be provided to operate the valve shaft within the scope of the present invention. A battery 31 may be received in the main compartment 21 of the housing 3 for powering the pump motor 25. A battery door 33 hingedly attached to the rear of the main compartment 21 closes the battery 31 within the compartment while providing access as needed. A bolt 35 holds the battery door 33 closed so that access to the battery 31 is normally blocked. Of course, a power source other than or in addition to a battery could be used.

A rotor (generally indicated at 37) is mounted on the rotor shaft 27 of the pumping unit 23 by a bolt 42. The rotor 37 includes an inner disk 39, an outer disk 41 and three rollers 43 (only one is shown) mounted between the inner and outer disks for rotation about their longitudinal axes relative to the disks. In the illustrated embodiment, the pump motor 25, rotor shaft 27 and rotor 37 may broadly be considered "a pumping device". It will be understood that peristaltic pumps that use mechanisms other than rollers may fall within the scope of the present invention. For example, a linear peristaltic pump could be used within the scope of the present invention. The roller 43 engages the administration feeding set 5, which is also received in first and second chutes (designated 45 and 47, respectively) formed on a faceplate 49 of the pumping unit 23 on which the pump motor 25 is also mounted. The first and second chutes 45, 47 receive portions of the administration feeding set 5, as will be described in more detail hereinafter. The door 7 covers the chutes 45, 47 and rotor 37 when it is closed as it is in FIG. 1. Other bolts 51 hold various components of the pump 1 together.

Figure 5:
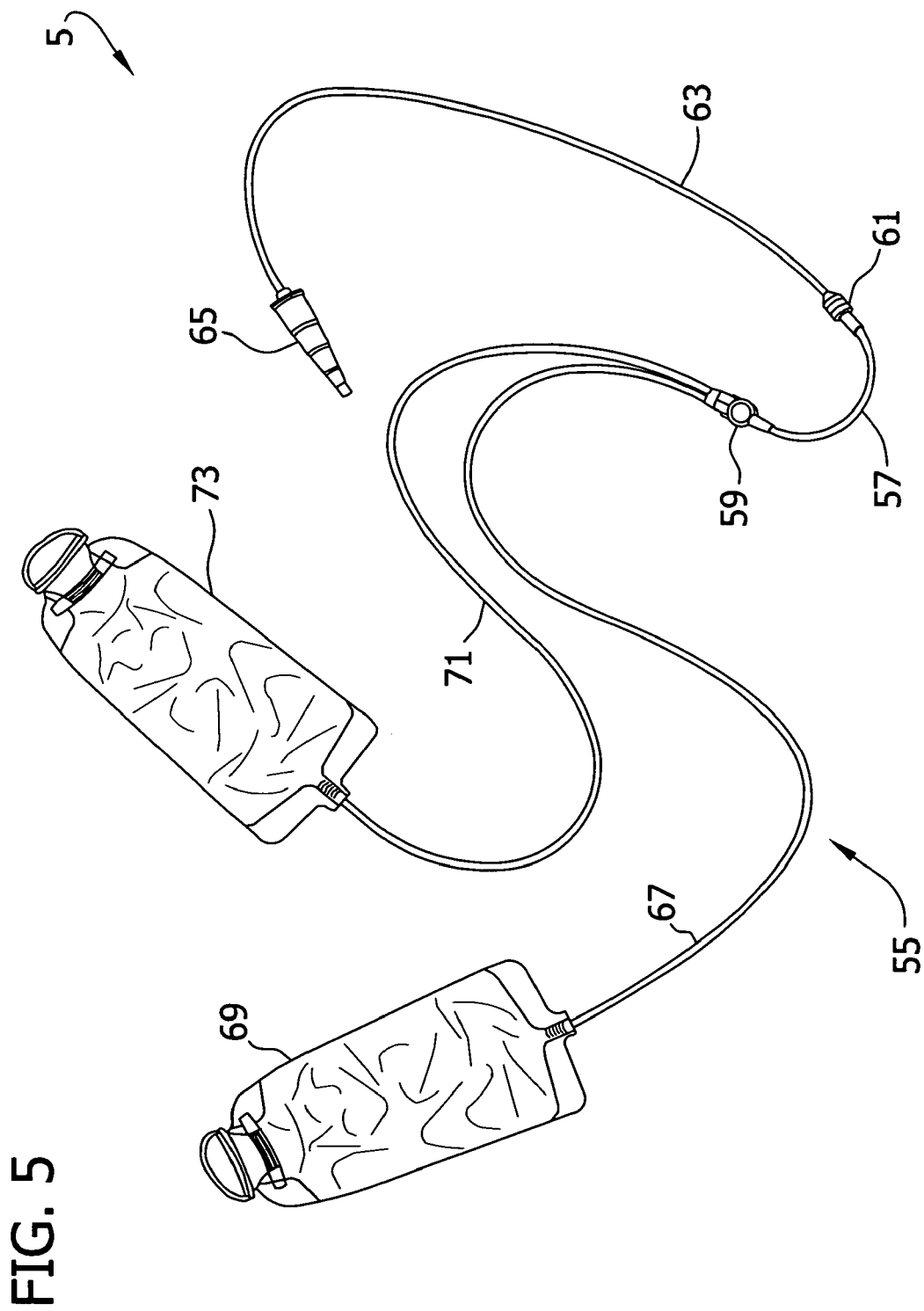
FIG. 5 is a perspective of the administration feeding set.

Referring now to FIG. 5, the administration feeding set 5 comprises tubing indicated generally at 55 that provides a fluid pathway between at least one source of fluid and a patient. Tubing 55 can be made of a medical grade, deformable silicone and comprises first tube section 57 connected between a valve mechanism 59 and mounting member 61. A second tube section 63 is connected to the mounting member 61 and at an outlet of the tubing 55 to a connector, such as a barbed connector 65, suitable for connection to a gastrostomy device (not shown) attached to a patient. Third tube section 67 is connected at an inlet of the tubing 55 to a bag 69 of feeding fluid and to valve mechanism 59, and fourth tube section 71 is connected at an inlet of the tubing 55 to a bag 73 of flushing fluid and to the valve mechanism. The valve mechanism 59 is operable to selectively permit flow of feeding fluid from bag 69 or flushing fluid from bag 73, or prevent any fluid flow communication from the feeding or flushing fluid bags 69, 73 into the first tube section 57. The valve mechanism 59 can be turned to three positions. The first closes off all fluid flow from the third and fourth tube sections 67, 71 to the first and second tube sections 57, 63, the second allows feeding fluid to flow from the bag 69 to the first and second tube sections, and a third allows flushing fluid to flow from bag 73 to the first and second tube sections. As previously stated, pump sets of different constructions may be used, for example a recertification set may be used to verify and/or correct the pump accuracy. The pump 1 can be configured to automatically recognize what kind of set is installed and to alter its operation to conform to that called for by the particular administration set. Still further, the pump 1 can be configured to recognize whether the first tube section 57 is properly installed on the pump. Examples of suitable pump sets (including valve mechanisms) are shown in co-assigned U.S. Ser. No. 10/853, 958 previously incorporated by reference.

In use, the administration feeding set feeding fluid bag 69 and flushing fluid bag 73 can be hung from a suitable support, such as an IV pole (not shown). The door 7 on the side of the pump 1 is swung open and the valve mechanism 59 can be placed in the first chute 45 so that the valve shaft 29 of the pump is engaged with the valve mechanism. Thus, rotation of the valve shaft 29 controls in which of the three positions the valve mechanism 59 is placed. The first tube section 57 is placed around the lower part of the rotor 37 and the mounting member 61 is placed in the second chute 47. The second chute is generally funnel-shaped so that the mounting member 61 can be placed into the chute 47 at a location in which the first tube section 57 is substantially stretched around the rotor 37. The first tube section 57 can relax slightly, pulling the mounting member 61 further down in the second chute 47. However, the first tube section 57 is maintained in a stretched condition around the rotor when properly installed on the pump 1. The door 7 can be re-closed to cover the first and second chutes 45, 47 and the rotor 37. The connector 65 at the end of the second tube section 63 can be connected to a conduit (not shown) attached to the patient in a known manner. It will be understood that any suitable connection to the patient for delivering the fluid may be used without departing from the scope of the present invention.

Figure 6:
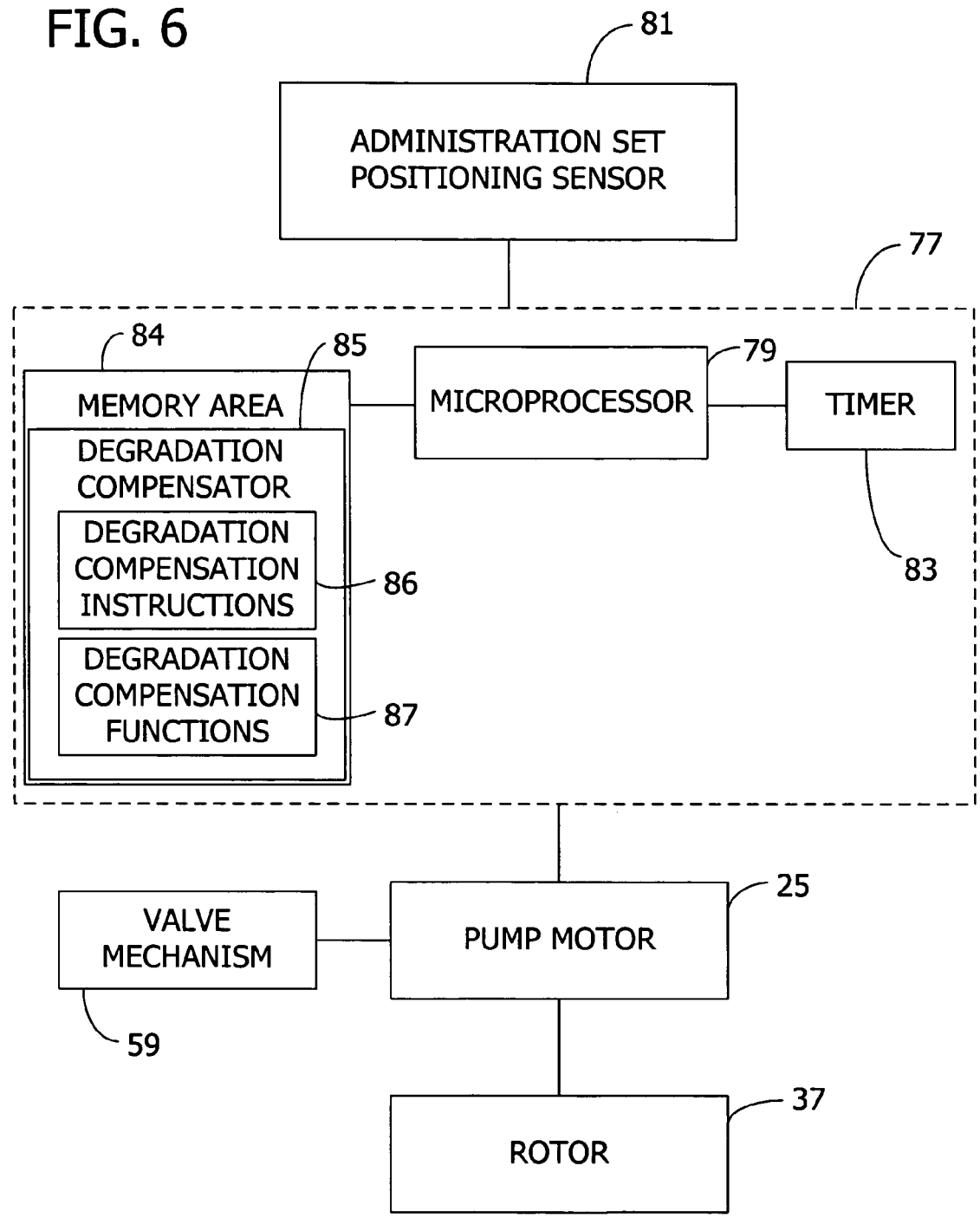
FIG. 6 is a block diagraph of the components of the enteral feeding pump.

The pump 1 can be programmed or otherwise controlled for operation in a desired manner. For instance, the pump 1 can begin operation to providing feeding fluids from bag 69 to the patient. The care giver may select (for example) the amount of fluid to be delivered, the rate at which the fluid is to be delivered and the frequency of fluid delivery. The pump 1 has a controller 77 (see, FIG. 6) including a microprocessor 79 that allows it to accept programming and/or to include pre-programmed operational routines that can be initiated by the care giver. The controller 77 is in communication with an administration set positioning sensor 81 that detects whether the administration feeding set 5 has been positioned properly, as previously described. Other sensors (not shown), such as a sensor that determines the type of administration set that has been placed in the pump 1 and a flow monitoring sensor can be in communication with the controller 77 to facilitate accurate operation of the pump. The controller 77 is also connected to the pump motor 25 for controlling its operation to actuate the valve mechanism 59 and the rotor 37. The pump motor 25 can operate the valve mechanism 59 and rotor 37 independently of each other.

If the pump 1 is to deliver feeding fluid from the bag 69 to the patient, the valve shaft 29 is rotated so that the valve mechanism 59 is moved to the second position in which fluid communication from the feeding fluid bag 69 to the first tube section 57 is open. The amount of feeding fluid that is delivered to the patient is controlled by the number of rotations of the rotor 37 (in a counterclockwise direction as viewed in FIG. 2). In the illustrated embodiment, the rotor 37 includes the three rollers 43 so that each one-third of a rotation delivers one aliquot of fluid to the patient. As each roller 43 first engages the first tube section 57, it pinches off the first tube section thereby closing off an amount of fluid forward (i.e., toward the patient) from the fluid coming from the feeding fluid bag 69. The roller 43 continues to the right, pushing fluid forward of the roller toward the patient. Finally, the roller 43 releases engagement with the first tube section 57 at about the same time the trailing roller engages the first tube section for pinching it off for delivering the next aliquot of fluid. Thus, when the microprocessor 79 receives a command to deliver a fluid flow rate, it calculates the number of rotations within a given period of time that will deliver a number of aliquots producing the desired flow rate. More specifically in the illustrated embodiment, the controller 77 determines the amount of time between rotations of the rotor 37. The amount of time between rotations is dependent upon the volume of the aliquots delivered in a single rotation. It is to be understood that other ways of changing rotor operation could be used to maintain a constant flow rate. It has been determined that if the microprocessor assumes that the volume of each aliquot is the same or varies only as a function of flow rate, this will lead to errors in the actual flow rate of fluid delivered.

Accordingly, the controller 77 of the present invention includes a timer 83 and a memory area 84 including an aliquot volume degradation compensator 85. In the illustrated embodiment, the degradation compensator 85 includes degradation compensation instructions 86 and degradation compensation functions 87. The timer 83 is initiated in a suitable manner when the administration feeding set 5 is first installed in the pump 1. The initiation is preferably automatic. For example, the timer 83 may initiate when the mounting member 61 is detected as being in the proper position for a certain period of time. Upon initiation, the timer 83 begins to count the amount of time the administration feeding set 5 has been in use. The degradation compensator 85 uses this information and the selected flow rate to compensate or correct the volume associated with each aliquot over the life of the administration feeding set 5. Thus, the microprocessor 79 can use a different aliquot volume amount over the life of the administration feeding set 5 to keep the flow rates delivered by the pump 1 substantially accurate.

The degradation compensator 85 operates to correct for time-dependent variation in the volume associated with each aliquot of fluid delivered by the pump 1 to the patient. However, the time-dependent variation is also dependent upon selected flow rate. More specifically, the controller 77 employs the following function to determine the volume in each aliquot:

$$H_i(x)=G_i(x)+T*F_i(x)$$

$G_i(x)$ is the established volume as a function of flow rate selected. T is the time of feeding set use and $F_i(x)$ is the administration set flow compensation of volume as a function of flow rate selected. The variable x is flow rate and $H_i(x)$ is the corrected aliquot volume as a function of flow rate selected and time. The equation has been established through testing and curve-fitting the data from the tests. It will be appreciated that flow rate shows up in the function $F_i(x)$ which is used to calculate time-dependent variations. $G_i(x)$ is independent of how long a particular administration feeding set has been in use, and can be a different equation depending upon the flow rate selected and is used from the very beginning of operation of the pump 1 to calculate aliquot volume. It is also possible that $G_i(x)$ can always be the same equation (regardless of flow rate) or a constant. For example, if the flow rate selected is low (e.g., a few milliliters per hour), then $G_i(x)$ may be constant, i.e., $G_i(x)=B$. At higher flow rates, the equation takes on a polynomial form that may vary depending upon the flow rate selected. The equation may be linear, e.g., mx+B, or non-linear, e.g., $Lx^2+mx+B$, where L and m are empirically determined coefficients and B is an empirically determined constant. The coefficients and equations are stored in the controller 77 so that when the flow rate is known, the microprocessor 79 can look up the associated equation and coefficients in, for example, a look up table in the controller memory. The flow rate is plugged into the selected equation $G_i(x)$ to find the aliquot volume compensation. Preferably, each equation $G_i(x)$ is operable over a range of flow rates.

The degradation compensator 85 provides computer-executable instructions 86 for use in calculating $T*F_i(x)$, and operates in a similar way as the microprocessor in calculating $G_i(x)$. The degradation compensator 85 looks at the selected flow rate and selects a previously stored function from a look up table or other source represented by the degradation compensation functions 87 in FIG. 6. However unlike the calculation of $G_i(x)$, the selected equation is multiplied by the time T the administration feeding set 5 has been in operation. In one embodiment, the time T increments once per hour, but any frequency of updating the time T may be used without departing from the scope of the present invention. It will be appreciated that even at high flow rates within a time in which T=0 (i.e., for a newly installed administration feeding set 5), the compensation of aliquot volume based on degradation of the dimensions of the administration feeding set over time is zero. Thus, initially the degradation compensator 85 has no affect on the calculation of aliquot volume because the pump set 5 is relatively dimensionally stable.

Figure 7:
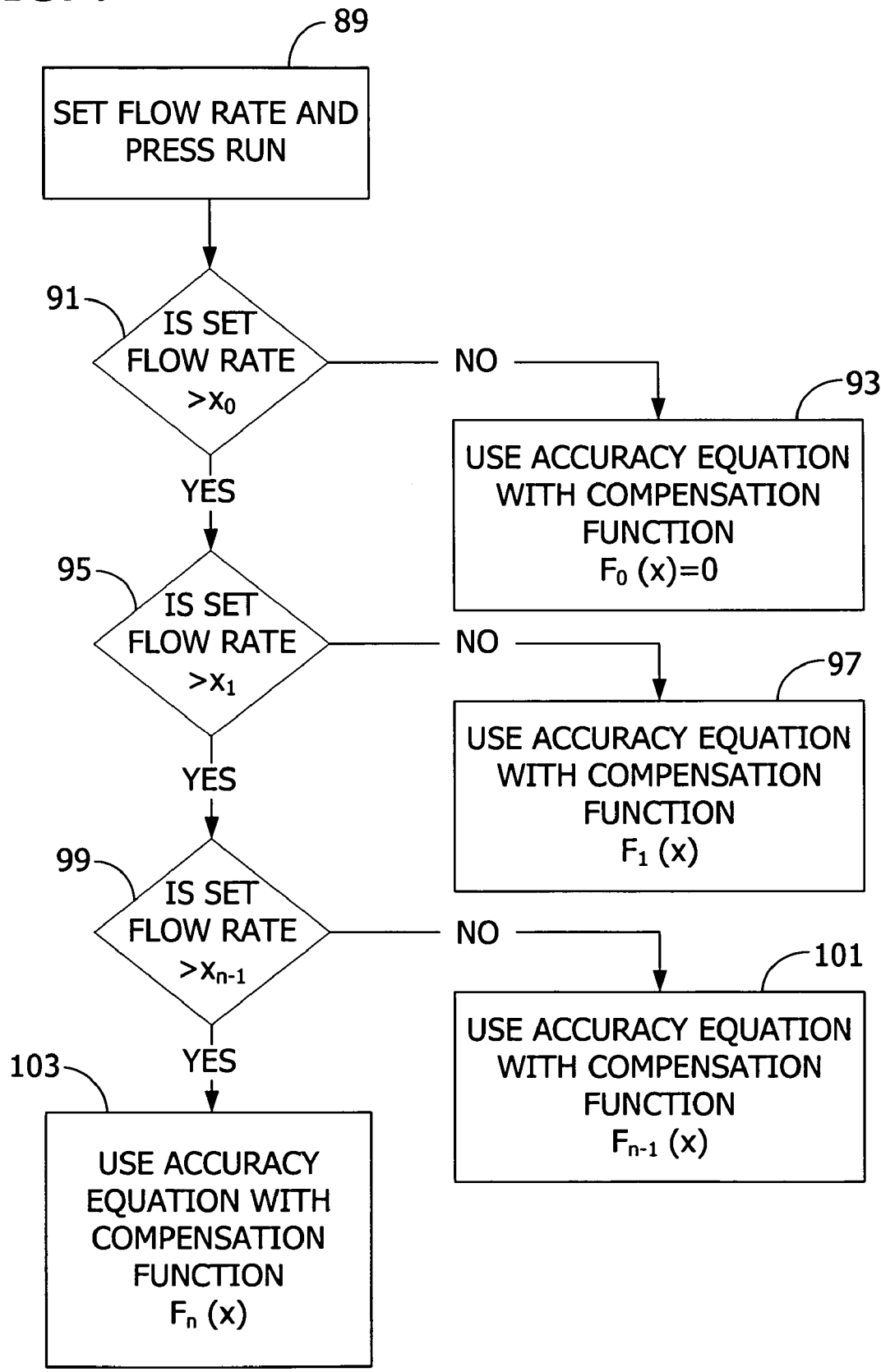
FIG. 7 is a flow chart of an aliquot correction routine.

Referring now to FIG. 7, the degradation compensation instructions 86 of the degradation compensator 85 used to account for time based variations in aliquot volume are shown. In other words, the flow chart shows how $T*F_i(x)$ is calculated. The degradation compensation instructions 86 are machine readable instructions on any suitable medium, broadly identified as the memory area 84. These instructions can be carried out by the microprocessor 79. After a particular flow rate x is selected at block 89, the degradation compensation instructions 86 first look at decision block 91 to see if the flow rate x is greater than some minimum threshold flow rate $x_0$ (e.g., 40 ml/hr). If the selected flow rate x is less than threshold $x_0$, $F_i(x)$ is set to zero at process block 93 and the aliquot volume calculation performed by the microprocessor becomes:

$$H_i(x)=G_i(x)$$

Therefore, no matter how long the administration feeding set 5 has been in operation, if the flow rate x is low enough, only the standard flow rate based function $G_i(x)$ is used. If the selected flow rate is greater than the threshold ($x_0$) in decision block 91, the program moves on to decision block 93 where it inquires whether the flow rate x is above a next higher threshold ($x_1$). If the flow rate x is less than $x_1$, then the degradation compensator 85 looks up the equation and coefficients and constants in the degradation compensation functions 87 that are associated with that particular flow rate threshold $x_1$. For example, the equation can be: $F_i(x)=Ax+N$, where A is a coefficient, N is a constant and x is the selected flow rate. The solution to this equation is multiplied by the time T to arrive at the time-dependent aliquot volume correction in process block 97. Other equations could be used for $F_i(x)$ depending upon their ability to model experimentally determined aliquot volume alteration over time and as a function of flow rate. For the embodiment described herein, the coefficients of the equations and the constants have been empirically determined (i.e., by curve-fitting test data) and are different for different selected ranges of flow rates.

If at decision block 95 the flow rate x is greater than the threshold $x_1$, then the instructions 86 proceed to the final decision block 99 which inquires whether the selected flow rate x is greater than the maximum threshold $x_{n-1}$. It will be appreciated that other decision blocks (not shown) prior to the maximum threshold decision block 99, and associated process blocks (not shown) providing different time-dependent aliquot volume corrections based on selected flow rate may be used without departing from the scope of the present invention. Similar to the prior steps, if the selected flow rate x is not above the (maximum) threshold $x_{n-1}$, the program at process block 101 applies a particular function $F_{n-1}(x)$ associated with that range of flow rates (i.e., above $x_{n-2}$ and below xn–1) from the degradation compensation functions 87, in a similar fashion as the prior process block 97. On the other hand, if the flow rate x exceeds the maximum threshold $x_{n-1}$, the degradation compensation instructions 86 move to process block 103 where a final compensation function Fn(x) is selected from the degradation compensation functions 87 for use in calculating the time based aliquot volume compensation. The flow rate $x_{n-1}$ above which this function $F_n(x)$ is employed may be at or near the maximum flow rate at which the pump 1 is capable of operating. As in all cases, the result of the equation $F_n(x)$ is multiplied by time T and added by the microprocessor 79 to the result of $G_n(x)$ to produce the aliquot volume $H_n(x)$. This aliquot volume amount can be used to signal the pump motor 25 to control the period of time between rotations of the rotor 37 to accurately deliver the desired flow rate of fluid.

Thus it may be seen that the various objects and features of the present invention are achieved by the embodiment of the pump 1 disclosed herein. The pump controller 77 has the degradation compensator 85 that allows the microprocessor 79 to compensate for changes in aliquot volume of the pump 1 based on flow rate, and also using a compensation factor for the amount of time the administration feeding set 5 has been in use. The time compensation factor is able to allow for the degradation (or simply changes) in the dimensions of the administration feeding set 5 over time. Therefore, the patient can receive accurate flow rates of fluid over the entire life of the administration feeding set (e.g., 24 hours).

Embodiments of the invention may be described in the general context of computer-executable instructions, such as program modules, executed by one or more computers or other devices. The computer-executable instructions may be organized into one or more computer-executable components or modules including, but not limited to, routines, programs, objects, components, and data structures that perform particular tasks or implement particular abstract data types. Aspects of the invention may be implemented with any number and organization of such components or modules. For example, aspects of the invention are not limited to the specific computer-executable instructions or the specific components or modules illustrated in the figures and described herein. Other embodiments of the invention may include different computer-executable instructions or components having more or less functionality than illustrated and described herein.

Further, the order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

In operation, microprocessor 79 of the controller 77 executes computer-executable instructions such as those illustrated in the figures to implement aspects of the invention. Aspects of the invention may also be practiced in distributed computing environments where tasks are performed by remote processing devices that are linked through a communications network. In a distributed computing environment, program modules may be located in both local and remote computer storage media including memory storage devices.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Moreover, the use of "up", "down", "top" and "bottom" and variations of these terms is made for convenience, but does not require any particular orientation of the components.

As various changes could be made in the above without departing from the scope of the invention, it is intended that all matter contained in the above description and shown in the accompanying drawings shall be interpreted as illustrative and not in a limiting sense.

What is claimed is:

1. A pumping apparatus for use with a pump set to deliver fluid through the pump set, the pumping apparatus comprising:

a pumping device capable of acting on the pump set to produce a fluid flow within the pump set, the pumping device producing said fluid flow in a series of aliquots;

a housing capable of receiving at least a portion of the pump set to be acted upon by the pumping device;

a controller programmed to control an electrical signal to the pumping device, the controller including a pump set degradation compensator for changing the electrical signal thereby altering operation of the pumping device whereby the fluid flow rate delivered by the pumping apparatus is more accurate over the useful life of the pump set, wherein the controller includes a memory and a microprocessor in communication with the memory;

wherein the pump set degradation compensator is a software program stored in the memory of the controller that is executable by the microprocessor and is configured to correct the aliquot volume as a function of feed rate selected and time of use of the pump set;

wherein the software program comprises the following equation:

Hi(x)=Gi(x)+T*Fi(x), where Gi(x) is the established aliquot volume as a function of flow rate selected, T is time of pump set use, Fi(x) is pump set flow compensation of volume as a function of flow rate selected, x is a user selected flow rate, and Hi(x) is the corrected aliquot volume as a function of flow rate selected and time of use of the pump set.

2. A pumping apparatus as in claim 1 further comprising an actuator having at least one pump set engaging member for engaging the pump set to force fluid to flow in the pump set.

3. A pumping apparatus as in claim 2 wherein the actuator comprises a rotor adapted to receive a portion of the pump set into engagement with the rotor.

4. A pumping apparatus as in claim 3, wherein there are plural engaging members, each engaging member comprising a roller for engaging the pump set and generating an aliquot of fluid flow.

5. A pumping apparatus as in claim 1, wherein the memory is selected from a group consisting of: random access memory, flash, EEPROM, PROM, or disk.

6. A pumping apparatus as in claim 1 wherein Gi(x) is one of a constant and a polynomial equation.

7. A pumping apparatus as in claim 1, wherein the established aliquot volume Gi(x) is at least one of: (i) a constant, the constant being B and stored in a lockup table; the table being indexed by user selected flow rate x; (ii) a linear function mx+B of the user selected flow rate; and (iii) a nonlinear equation Lx2+mx+B, wherein L is an empirically established constant for a user selected flow rate x, the value of L for a plural of flow rate x are stored in a table in the memory.

8. A pumping apparatus as in claim 7, wherein the constant B is an empirically established constant for the user selected flow rate x or a range thereof and stored in a table in the memory.

9. A pumping apparatus as in claim 7 further comprising an input device operatively connected to the memory communicates user inputs for x.

10. A pumping apparatus as in claim 7, wherein m in the linear function is an empirically established constant for a user selected flow rate x; the values of m for a plurality of user flow rates x are stored in a table in the memory.

11. A pumping apparatus as in claim 1 wherein Fi(x) is one of a constant and a polynomial.

12. A pumping apparatus as in claim 11 wherein the Fi(x) is a linear function Ax+N, where A as a coefficient and N is a constant selected from the memory based on the flow rate x selected by a user.

13. A pumping apparatus as in claim 1 in combination with the pump set, and wherein the pump set is disposable.

14. A pumping apparatus as in claim 1 in combination with the pump set, wherein the pump set includes at least two tube sections.

15. A pumping apparatus as in claim 1 wherein the memory includes a lockup table accessible by the microprocessor, the lookup table including a plurality of different equations for the established aliquot volume Gi(x), wherein the equations are selectable by the microprocessor based on the user selected flow rate x.

16. A method of delivering accurate flow rates of fluid using a pumping apparatus that acts on a pump set attached to the pumping apparatus to produce flow of fluid in aliquots, the method comprising:
determining the amount of time the pump set has been in use in the pumping apparatus;
calculating the volume of fluid in each aliquot delivered by the pumping apparatus including executing instructions that are capable of correcting the aliquot volume based on the amount of time the pump set has been in use in the pumping apparatus, wherein said calculating the volume of the fluid in each aliquot is calculated by a microprocessor executing a software program comprising the following equation:

$$Hi(x)=Gi(x)+T*Fi(x)$$

where Gi(x) is the established volume as a function of flow rate selected; T is the amount of time of pump set use; Fi(x) is pump set flow compensation of volume as a function of flow rate selected; x is flow rate and Hi(x) is the corrected aliquot volume as a function of flow rate selected and time; operating the pumping apparatus to deliver a number of aliquots having the aliquot volume determined in the preceding step to maintain a selected flow rate.

17. A method as in claim 16 further comprising inputting the flow rate of fluid to be delivered into memory associated with the pumping apparatus.

18. A method as in claim 16 wherein Gi(x) is one of a constant and a polynomial.

19. A method as in claim 18 wherein Gi(x) is at least one of: (i) a linear function of selected flow rate Gi(x)=mx+B, where m is a coefficient and B is a constant; (ii) a constant B; and (iii) a nonlinear function of selected flow rate Gi(x)=Lx2+mx+B, where L and m are coefficients corresponding to particular selected flow rate and stored in memory and B is a constant corresponding to a particular flow rate and stored in memory.

20. A method as in claim 16 wherein Fi(x) is one of a constant and a polynomial.

21. A method as in claim 20 wherein Fi(x) is a linear function Fi(x)=Ax+N, where A is a coefficient and N is a constant selected from the memory based on the flow rate x selected by a user.

22. A method as in claim 16 wherein one or more computer-readable media have computer executable instructions executed by the microprocessor for performing the method of claim 16.

23. A method as in claim 16 wherein the established volume Gi(x) is an equation selected by the microprocessor from a lookup table in a memory of the pumping apparatus, wherein the lookup table includes a plurality of different equations that are selectable by the microprocessor based on the flow rate x.

* * * * *